(12) United States Patent
Lee et al.

(10) Patent No.: US 11,446,667 B2
(45) Date of Patent: Sep. 20, 2022

(54) INTEGRATED MOLECULAR DIAGNOSTICS SYSTEM (IMDX) AND METHOD FOR DENGUE FEVER

(71) Applicant: THE REGENTS OF THE UNIVERSITY OF CALIFORNIA, Oakland, CA (US)

(72) Inventors: Luke P. Lee, Orinda, CA (US); Jun Ho Sun, El Cerrito, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 539 days.

(21) Appl. No.: 16/380,693

(22) Filed: Apr. 10, 2019

(65) Prior Publication Data
US 2019/0299207 A1    Oct. 3, 2019

Related U.S. Application Data (63) Continuation of application No. PCT/US2017/056139, filed on Oct. 11, 2017.

(60) Provisional application No. 62/406,694, filed on Oct. 11, 2016.

(51) Int. Cl.
| | |
|---|---|
| *C12Q 1/68* | (2018.01) |
| *B01L 3/00* | (2006.01) |
| *C12N 5/078* | (2010.01) |
| *C12Q 1/686* | (2018.01) |
| *C12Q 1/6834* | (2018.01) |
| *C12Q 1/70* | (2006.01) |
| *B01L 7/00* | (2006.01) |

(52) U.S. Cl.
CPC ......... *B01L 3/50851* (2013.01); *B01L 3/5027* (2013.01); *B01L 3/502715* (2013.01); *B01L 3/502753* (2013.01); *B01L 3/502761* (2013.01); *C12N 5/0641* (2013.01); *C12Q 1/686* (2013.01); *B01L 7/52* (2013.01); *B01L 2200/10* (2013.01); *B01L 2300/0681* (2013.01); *B01L 2300/0816* (2013.01); *B01L 2300/0874* (2013.01); *B01L 2300/0877* (2013.01); *B01L 2300/0883* (2013.01); *B01L 2300/0887* (2013.01); *B01L 2300/12* (2013.01); *B01L 2300/1861* (2013.01); *B01L 2400/0406* (2013.01); *C12Q 1/6834* (2013.01); *C12Q 1/701* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2009/0186357 A1 | 7/2009 | Mauk | |
| 2011/0111987 A1* | 5/2011 | Siegrist | B01L 3/5027 506/39 |
| 2011/0312699 A1* | 12/2011 | Azimi | F16K 99/003 506/39 |

FOREIGN PATENT DOCUMENTS

| | | |
|---|---|---|
| WO | 2016044532 | 3/2016 |
| WO | 2016115542 | 7/2016 |
| WO | 2018071541 | 4/2018 |

OTHER PUBLICATIONS

Wang et al. (Int J of Nanomedicine, 2012:7, 5019-5028 (Year: 2012).*
Wang et al. (Chem Eur J 2010, 16:5600-5606 (Year: 2010).*
Sun et al. (Chem Soc Rev, 2014, 43:6329) (Year: 2014).*
Son et al. (Light: Science & Applications 2015, 4:e280, p. 1-7) (Year: 2015).*
ISA/KR, Korean Intellectual Property Office (KIPO), International Search Report and Written Opinion dated Jan. 29, 2018, related PCT international application No. PCT/US2017/056139, pp. 1-19, claims searched, pp. 20-24.
Kang, Tae-Goo et al., "Single chip integrated viral RNA extraction and RT-PCR for infectious disease identification from blood sample", 14th International Conference on Miniaturized Systems for Chemistry and Life Sciences, Oct. 3-7, 2010, Groningen, The Netherlands, pp. 824-826.
Cao, Qingqing et al., "Microfluidic chip for molecular amplification of influenza A RNA in human respiratory specimens", PLoS One, 2012, vol. 7, Issue No. 3, e33176, published online Mar. 22, 2012, pp. 1-11.
Japanese Patent Office (JPO), Notice of Reasons for Refusal dated Jul. 19, 2021, related Japanese patent application No. 2019-519700, pp. 1-3, machine translation, pp. 4-6, claims, pp. 7-11.
Japan Patent Office (JPO), final rejection dated May 16, 2022, related Japanese patent application No. 2019-519700, Japanese-language document pp. 1-2, English-language translation, pp. 3-4, claims examined, pp. 5-8.

* cited by examiner

*Primary Examiner* — Stephanie K Mummert
(74) *Attorney, Agent, or Firm* — O'Banion & Ritchey LLP; John P. O'Banion (57) ABSTRACT

An integrated molecular diagnostics system (iMDx) for the detection of Dengue Fever at point-of-care, wherein blood plasma separation for the selective separation of the Dengue virus from the whole blood, LED-driven photothermal lysis of the Dengue virus for the RNA extraction, and LED-driven rapid optical cavity PCR for the amplification of Dengue viral RNA are integrated on-chip within a single microfluidic device.

10 Claims, 9 Drawing Sheets

INTEGRATED MOLECULAR DIAGNOSTICS SYSTEM (IMDX) AND METHOD FOR DENGUE FEVER

CROSS-REFERENCE TO RELATED APPLICATIONS

This application claims priority to, and is a 35 U.S.C. § 111(a) continuation of, PCT international application number PCT/US2017/056139 filed on Oct. 11, 2017, incorporated herein by reference in its entirety, which claims priority to, and the benefit of, U.S. provisional patent application Ser. No. 62/406,694 filed on Oct. 11, 2016, incorporated herein by reference in its entirety. Priority is claimed to each of the foregoing applications.

The above-referenced PCT international application was published as PCT International Publication No. WO 2018/071541 A1 on Apr. 19, 2018, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to diagnostic systems and methods, and more particularly to an on-chip detection system for point-of-care diagnosis of viral infections.

2. Background Discussion

Dengue Fever (DF) is a tropical febrile disease caused by the DENV virus. This positive sensed 11 kb ssRNA virus belongs to the Flaviviridae family and encompasses 4 serotypes DEN-1, DEN-2, DEN-3 and DEN-4. The different serotypes share the same disease symptoms (and 60-75% of genome) but catching one type does not immunize a person against the three other types. On the contrary, the emergence of a previously not encountered serotype in a region is often synonym to a vague of dengue fever.

DF is a mosquito-borne disease (mosquito genus: *Aedes*) which explains its prevalence in mainly tropical countries. There are an estimated 50 to 100 million cases annually of DF with 500'000 cases of the more severe form of DF. While the fatality rate of severe DF is around 20% if untreated, it can be lowered below 0.1% when the patient is in medical care.

The diagnostic of DF versus other fever inducing diseases is thus essential for the medical staff to allow careful monitoring of plasma leakage and other severe DF symptoms. Furthermore, discerning DF from other febrile diseases is important to monitor the outbreak of DF and take appropriate measures for the population at risk.

There are three different categories of possible targets in the bloodstream for diagnostic methods: the virus itself, the proteins produced by the infected cells (NS1) and the proteins produced by the human body in reaction to the infection (IgM, IgG, etc.). NS1, IgM and IgG have very different concentration and assay sensitivities depending on whether it is a first or secondary infection. It is therefore of interest to target the viruses themselves by means of the fastest viral RNA detection method: Real Time Polymerase Chain Reaction (RT-PCR).

A number of RT-PCR assays have been developed to detect and serotype DENV off-chip in the last 20 years. However, evaluations of published methods have shown a lack of sensitivity and/or specificity demanding improvement for 80% of the methods. Recently, several assays have been commercialized and have showed sensitivities between 83.3-100% and 100% specificity. They are, however, only operative in clinical settings or hospital.

Accordingly, an object of the present disclosure is a molecular diagnostic platform to detect viral RNA by RT-PCR in blood samples at point-of-care.

BRIEF SUMMARY

The technology of the present disclosure is directed to an integrated molecular diagnostics system (iMDx) for the detection of Dengue Fever at point-of-care. In one embodiment, blood plasma separation for the selective separation of the Dengue virus from the whole blood, LED-driven photothermal lysis of the Dengue virus for the RNA extraction, and LED-driven rapid optical cavity PCR for the amplification of Dengue viral RNA are integrated on-chip within a single device. By integrating these components, the time, cost and steps for the diagnosis of the Dengue fever can be significantly reduced, with excellent limit of detection, comparable to the clinically relevant concentration of the Dengue virus. With can also obtain sensitive, fast, and low cost iMDx for the point-of-care diagnosis of Dengue Fever.

The technology can be easily used for the detection of Dengue Fever at point-of-care via the nucleic acids amplification of viral particles using the polymerase chain reaction (PCR) or isothermal amplification such as loop-mediated isothermal amplification (LAMP), and recombinase polymerase amplification (RPA). Also, any viral diseases such as HIV, Ebola, and West Nile virus can be detected using the technology.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

DETAILED DESCRIPTION

FIG. 1A through FIG. 6 are directed to a technology for rapid and sensitive diagnosis of the Dengue Fever (DF) at point-of-care. One particular advantage of this technology is that it provides a sample-to-answer molecular diagnostics system to detect Dengue Fever using integrated on-chip sample preparation and detection via nucleic acids amplification with minimal steps. Additional advantages may include fast, sensitive and low-cost diagnostics at resource-limited settings. While systems and methods are particularly suited for fast and sensitive detection of the Dengue Fever, it is appreciated that other medical conditions, and any viral disease, such as, but not limited to, Ebola, HIV, and West Nile virus, can be detected using the technology of the present description.

Figure 1A:
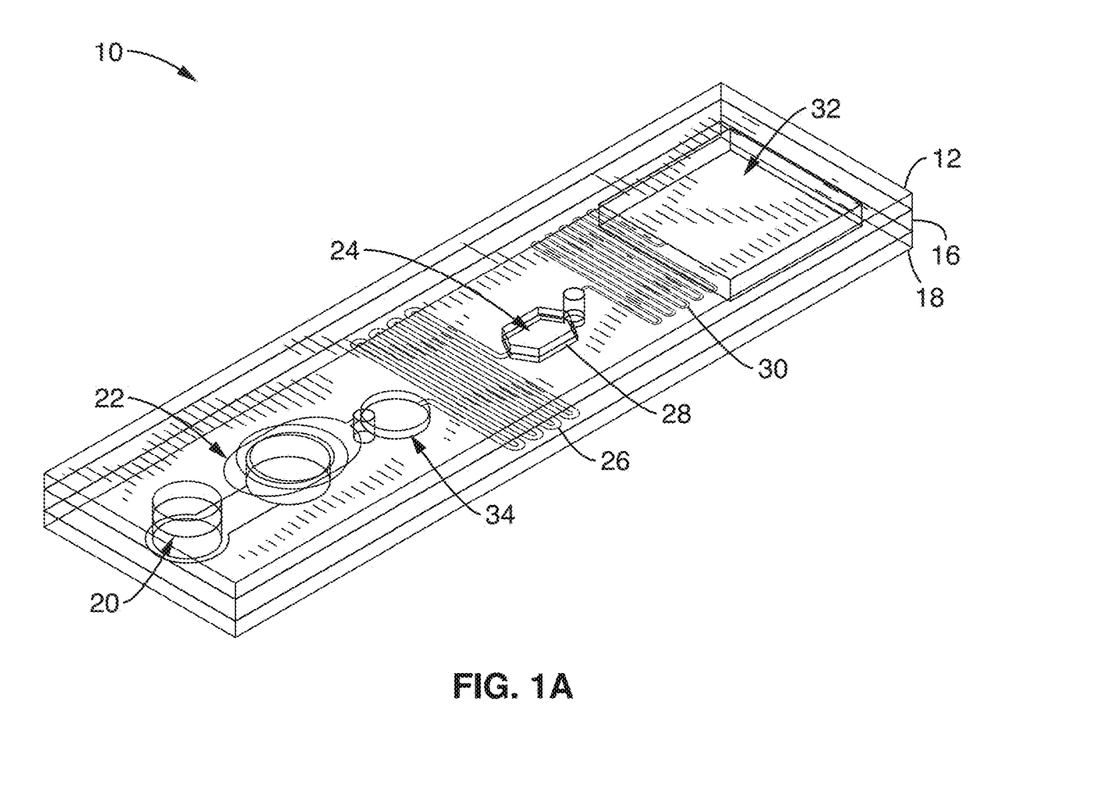
FIG. 1A shows a perspective schematic diagram of an integrated molecular diagnostics system (iMDx) for the detection of diseases such as Dengue Fever in accordance with the present description.
Figure 1B:
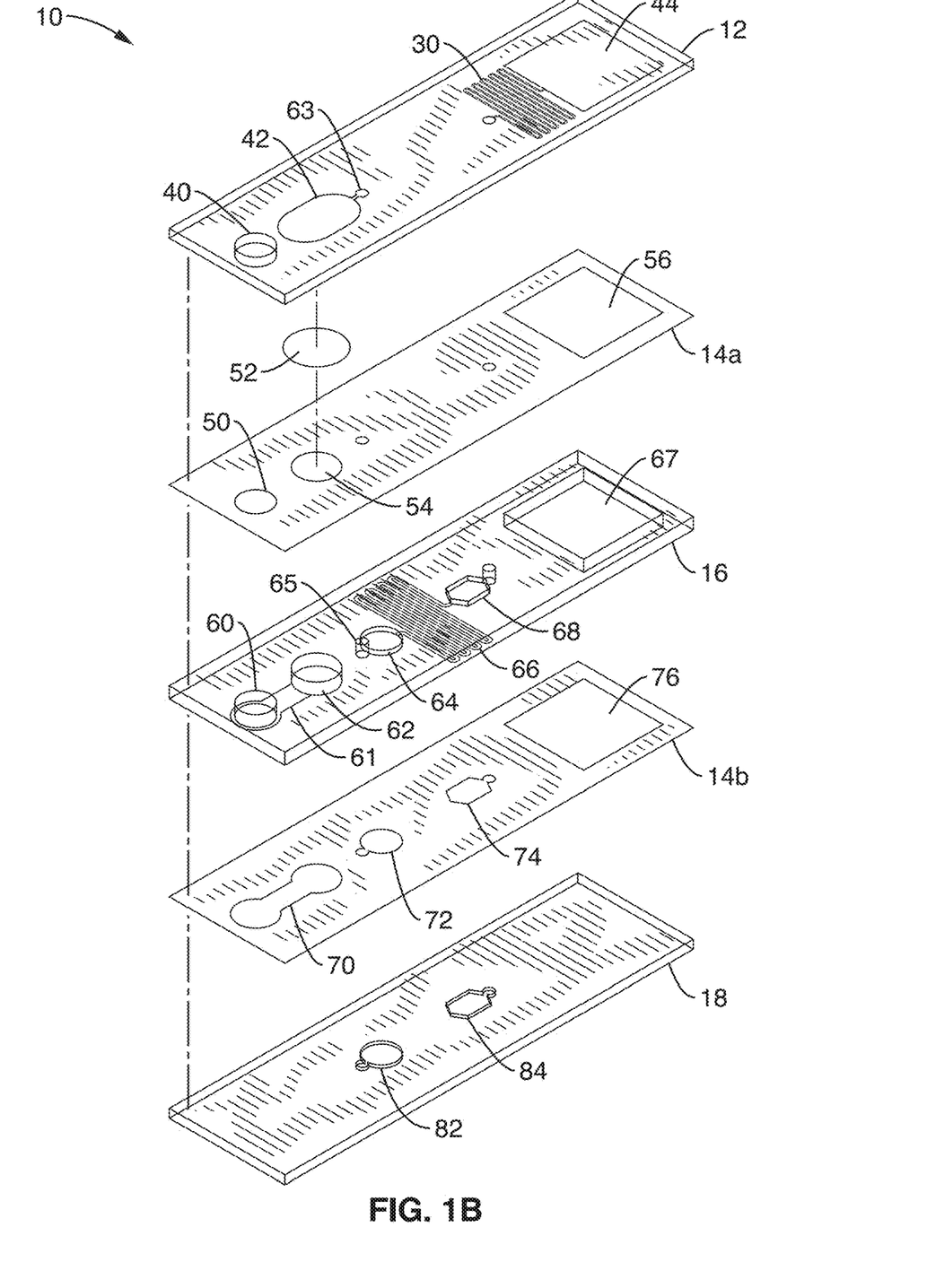
FIG. 1B shows a perspective schematic diagram of the individual layers of the iMDx system of FIG. 1A.

Referring now to FIG. 1A and FIG. 1B, FIG. 1A shows a perspective schematic diagram of an integrated molecular diagnostics system 10 (iMDx) for the detection of diseases such as Dengue Fever, and FIG. 1B shows a perspective schematic diagram of the individual layers of the iMDx system of FIG. 1A.

The iMDx system 10 comprises a multi-layer chip composed of a top layer 12, middle layer 16 and bottom layer 18 that are adhered together via bonding layers 14a and 14b. In one embodiment, the top layer 12, middle layer 16 and bottom layer 18 comprise a polymer such as polymethyl methacrylate PMMA), and bonding layer comprise a pressure sensitive adhesive (PSA), e.g. double-sided pressure sensitive adhesive (dsPSA) that is laser cut according to the specified pattern to appropriately bond each of the three layers 12, 16 and 18. However, it is appreciated that other polymers or materials available in the art may be used as appropriate. In such embodiment, the top layer 12 and middle layer 16 are injection molded at a thickness of 1 mm and 2 mm respectively, while the bottom layer 18 is laser cut at 0.8 mm thick.

Sample blood is administered into the iMDx system 10 at inlet 20. The blood plasma containing the target virus is first separated via separation compartment 22 using a hemolysis-free blood plasma separation method. Then, the separated blood plasma is heated via heating compartment 34 to extract the viral RNA from the virus by the LED-driven photothermal lysis. By using on-chip thermal lysis, the time, cost and steps to extract viral RNA is significantly reduced compared to the conventional off-chip RNA extraction kit. Finally, the extracted viral RNA is amplified via on-chip LED-driven rapid optical cavity PCR compartment 24. Each of the compartments 22, 24, and 34 are variably formed via features in layers 12, 16, and 18, the details of which are described in the following text.

Blood inlet 20 comprises a first aperture 40 win top layer 12 and a thru hole 60 in the middle layer 16 that forms a receiving well with bottom surface defined by bottom layer 18. Apertures 50 and 70 in respective bonding layers 14a and 14b allow for fluid communication between layers. Thru hole 60 is in fluid communication with thru hole 62 in middle layer 16 via a connecting channel 61 between holes 60 and 62. Thru hole 62 forms a second receiving well for the blood separation compartment 22.

In one embodiment, blood separation is achieved via a filter 52 that is disposed between the middle layer 16 and top layer 12 (over aperture 54 in bonding layer 14b). The filter comprises a porous material (e.g. polyester) having a pore size (e.g. 0.4 µm) that restricts red blood cells from passing upward, thus providing a filtered blood plasma into the compartment 22. In an alternative embodiment, other filtering configurations may be used in combination with or in place of filter 52. For example, blood plasma separation compartment 22 may comprise a micro-cliff structure 42 that uses a mechanism of suspension skimming is based on gravity induced sedimentation, similar to that described in U.S. patent application Ser. No. 15/017,851 filed on Feb. 8, 2016, herein incorporated by reference in its entirety. Separation of plasma and blood cells in whole blood can be essential for both protein detection and nucleic acid assays. For example, the hemoglobin in red blood cells can obscure optical readouts because of its opaqueness. Hemoglobin is also a well-known NA amplification inhibitor as the chelating properties disrupt the ion concentrations in the sample and thus inhibit polymerase activity.

The separated blood plasma then proceeds through apertures 63 and 65 in respective top layer 12 and middle layer 16 to holding well 64 formed in middle layer 16 of the heating compartment 34. In a preferred embodiment, heating compartment 34 comprises an on-chip heating element 82 formed as a metallic layer disposed on the upper surface of bottom layer 18. Heating element 82 may be coupled to a power source (e.g. battery, not shown) to provide electrical current to the element 82. In a preferred embodiment, the separated blood plasma is heated via heating compartment 34 as an optical cavity in middle layer 16 to extract the viral RNA from the virus by the LED-driven photothermal lysis in conjunction with channels 66 and indicator 26. More detail for the LED/optical cavity may be found with reference to U.S. Patent Nos. PCT/US2016/044255 and PCT/US2016/013732, herein incorporated by reference in their entirety.

The channels 66 are in communication with chamber 68 in the middle layer 16, upon which blood is drawn into to perform optical cavity PCR amplification. PCR amplification compartment 24 comprises an on-chip heating element 84 formed as a metallic layer disposed on the upper surface of bottom layer 18. PCR amplification compartment 24 and chamber 68, may be constructed as a micro-fluidic thermal cycling chamber such that heating element 84 forms an LED to facilitate a plasmonic photothermal light-to-heat conversion, for example similar to the LED driven plasmonic heating device and methods disclosed in U.S. application Ser. No. 15/649,328, filed on Jul. 13, 2017, herein incorporated by reference in its entirety.

In addition to nucleic acids amplification of viral particles using the polymerase chain reaction (PCR), it is appreciated the amplification compartment may be configured for isothermal amplification such as loop-mediated isothermal amplification (LAMP), or recombinase polymerase amplification (RPA)

In a preferred embodiment, heating elements 82, 84 comprise thin gold films that are deposited by the electron-beam evaporation to form an optical cavity for the photothermal lysis and PCR amplification of target nucleic acids. Cutouts 72 and 74 in bonding layer 14b provide apertures to the respective optical cavities.

A plurality of channels 30 are disposed in top layer 12 to be in fluid communication with PCR amplification compartment 24 for digitization of the sample for sample analysis in the form of quantitative digital detection of the blood composition. The data acquired using the iMDx system 10 is comparable to that which a costly thermal cycler, microplate spectrophotometer or other complex reader could provide. However, the iMDx system 10 costs only a few dollars to construct and perform. In one embodiment, by reading the endpoint result, it is possible to count the number of positive wells fluorescing, yielding the concentration data. A simple fluorescence and an endpoint count of positive wells can be done by a Smartphone with filters (not shown).

Finally, a cavity 32 may be formed in a recess 44 in top layer 12, as well as rectangular cutouts 56, 65 and 76 in intermediate layers, 14a, 16 and 14b, respectively. Cavity 32 is in communication with channels 30 and is configured to comprise or house a fluid biasing device or pump (not shown) used to draw the sample from inlet 20 through the various on-chip compartments.

By integrating these three components (separation compartment 22, heating compartment 34, and PCR amplification compartment 24) into a single device, a sample-to-answer lab on a chip device is obtained for point-of-care testing.

Example 1

Figure 2A:
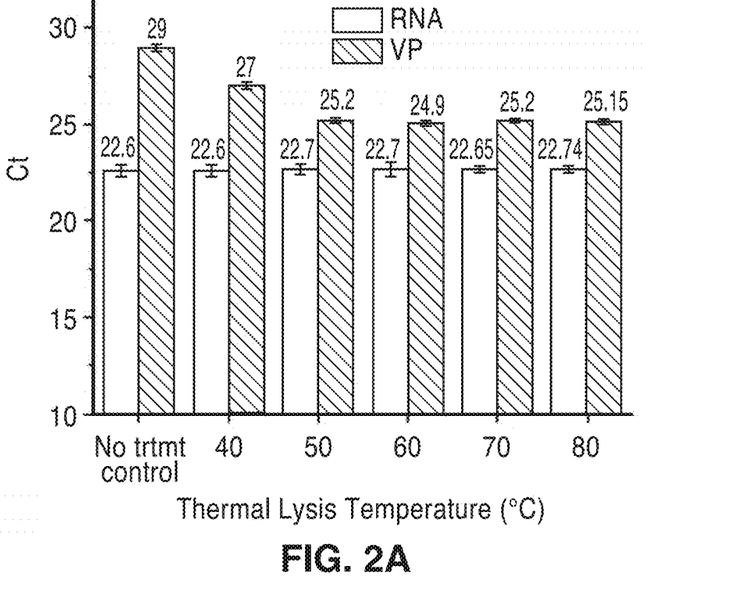
FIG. 2A is a plot showing a comparison of threshold cycle ($C_t$) for the RT-qPCR between the extracted RNA and thermally lysed Dengue viral particle (VP) as a function of temperature for the thermal lysis of Dengue virus. Thermal lysis was performed for 10 min at given temperatures.
Figure 2B:
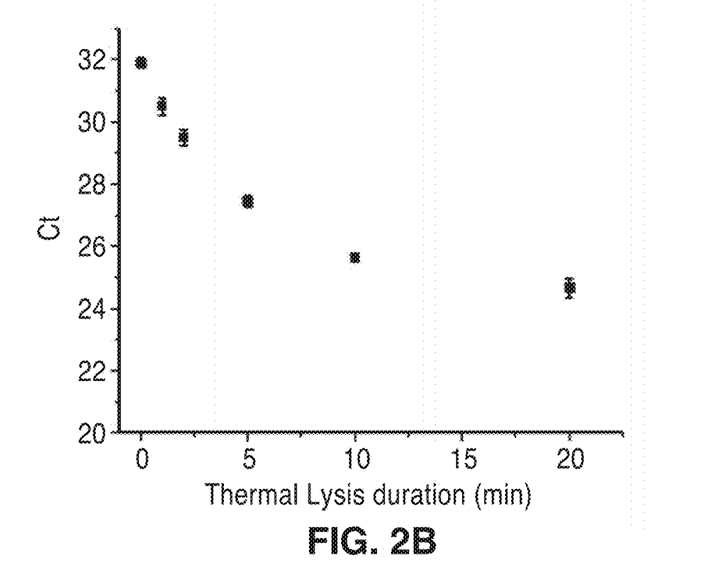
FIG. 2B is a plot showing changes of threshold cycle ($C_t$) for the RT-qPCR as a function of time for the thermal lysis.
Figure 2C:
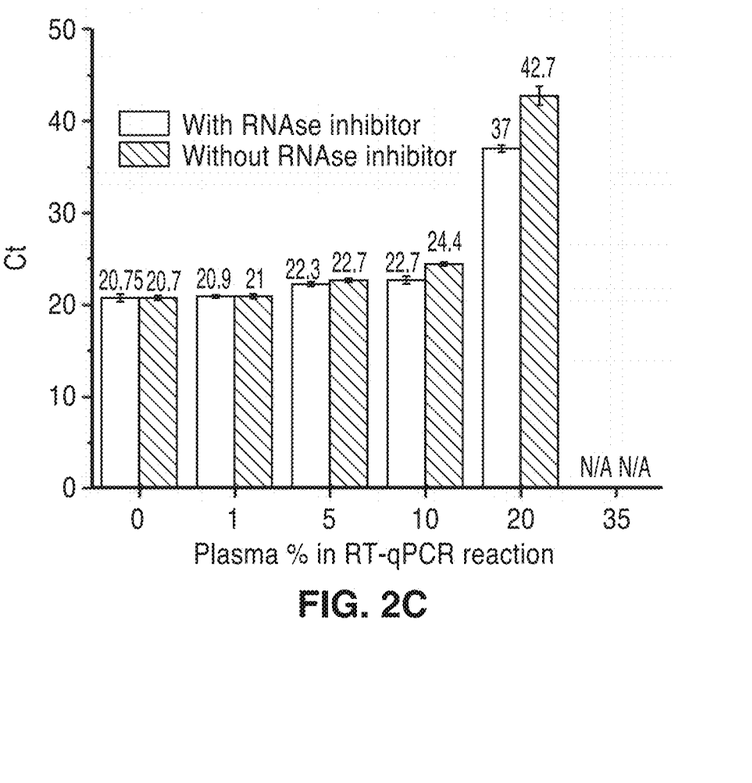
FIG. 2C is a plot showing a comparison of threshold cycle ($C_t$) for the RT-qPCR with and without RNAse inhibitor as a function of percentages of blood plasma for the reaction volume of RT-qPCR.
Figure 2D:
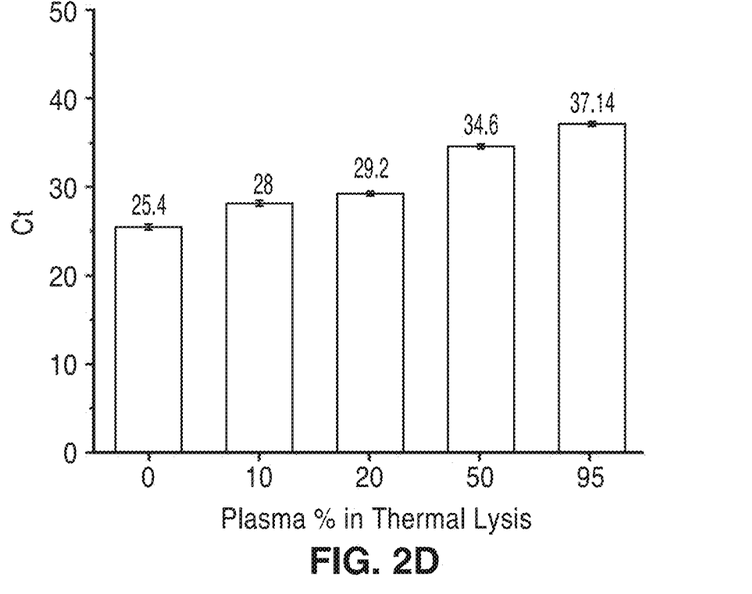
FIG. 2D is a plot showing changes of threshold cycle ($C_t$) for the RT-qPCR as a function of percentages of blood plasma during the thermal lysis of Dengue virus.

First, the temperature and time for the thermal lysis to extract the viral RNA from the Dengue virus were optimized as shown in FIG. 2A and FIG. 2B. As the temperature and time increase for the thermal lysis, the threshold values ($C_t$) are decreased at certain temperature (50° C.) and time (10 minutes), although the $C_t$ for the thermal lysis are still higher than the extracted RNA. This could be attributed to the RNA damage caused by the formaldehyde inactivation of Dengue virus. The effects of the percentages of the blood plasma during RT-qPCR and thermal lysis were investigated as shown in FIG. 2C and FIG. 2D. With 20% of blood plasma, the RT-qPCR was significantly inhibited, showing high threshold cycle, although the RNAse inhibitor was included during the reaction. Also, as the percentages of the plasma increase during thermal lysis, the threshold value is increased. Therefore, to obtain single step Dengue Fever on-chip detection without compromising the sensitivity, the maximum percentage of blood plasma during thermal lysis as well as RT-PCR is around 10%, based on these results.

Figure 3:
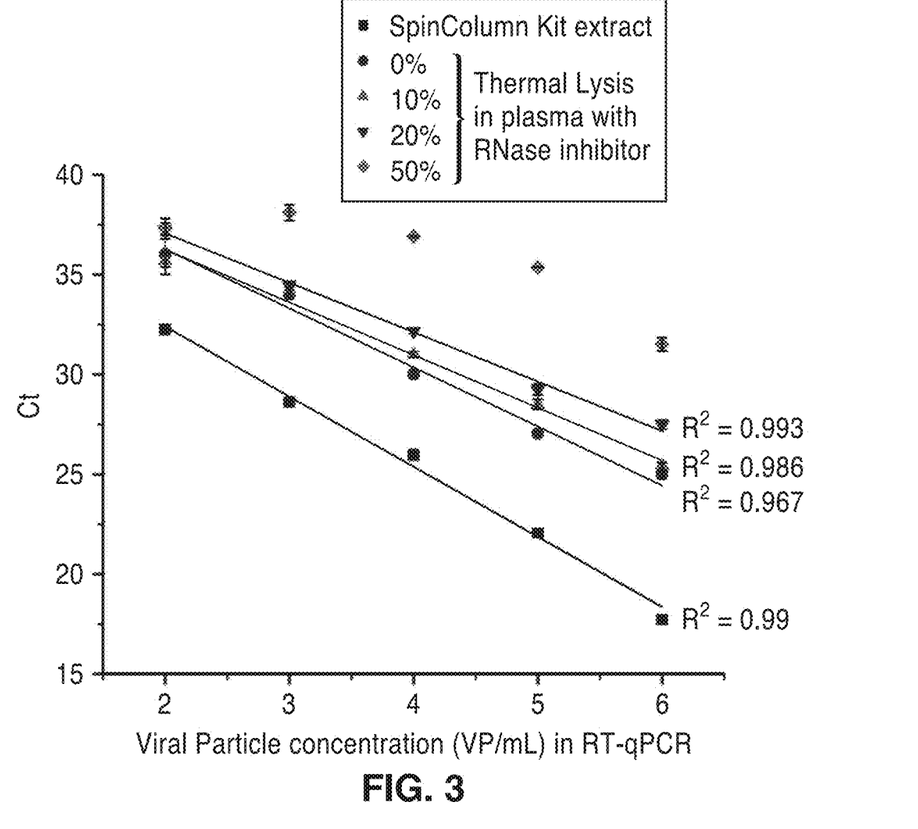
FIG. 3 is a plot summarizing the threshold cycles ($C_t$) for the RT-qPCR of thermally lysed Dengue virus with different percentages of blood plasma during thermal lysis of Dengue virus.

FIG. 3 shows a summary of the threshold cycles ($C_t$) for the RT-qPCR of the viral RNA extracted by the thermal lysis of the Dengue virus as a function of percentages of the blood plasma during the thermal lysis. Although the threshold cycles are increased with increase of blood plasma, the calibration curves show good $R^2$ values.

Example 2

Figure 4A:
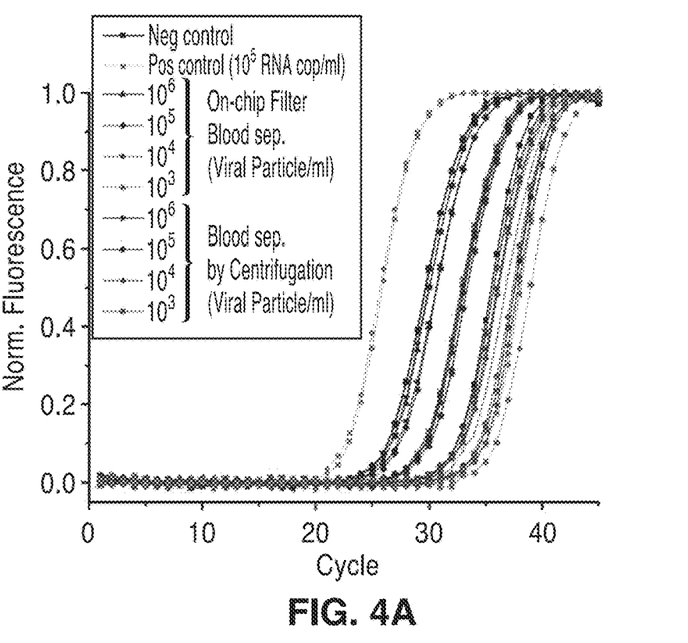
FIG. 4A is a plot showing real-time fluorescent intensities for the RT-qPCR using blood plasma spiked with different concentrations of the Dengue viral particles. The blood plasmas were separated by the conventional centrifugation method and on-chip blood plasma separation device in accordance with the present description.
Figure 4B:
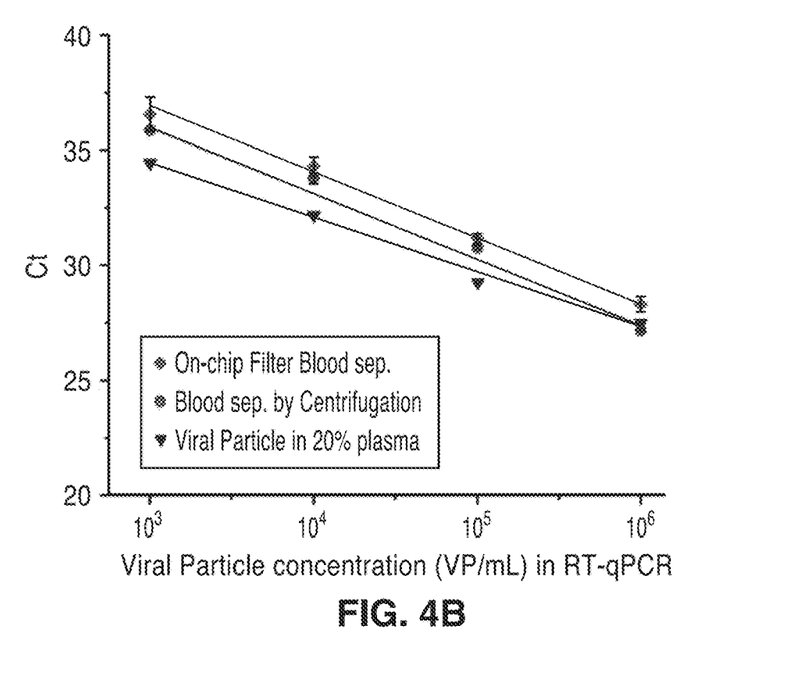
FIG. 4B is a plot summarizing the threshold cycle ($C_t$) for the RT-qPCR using blood plasma prepared with different methods.
Figure 4C:
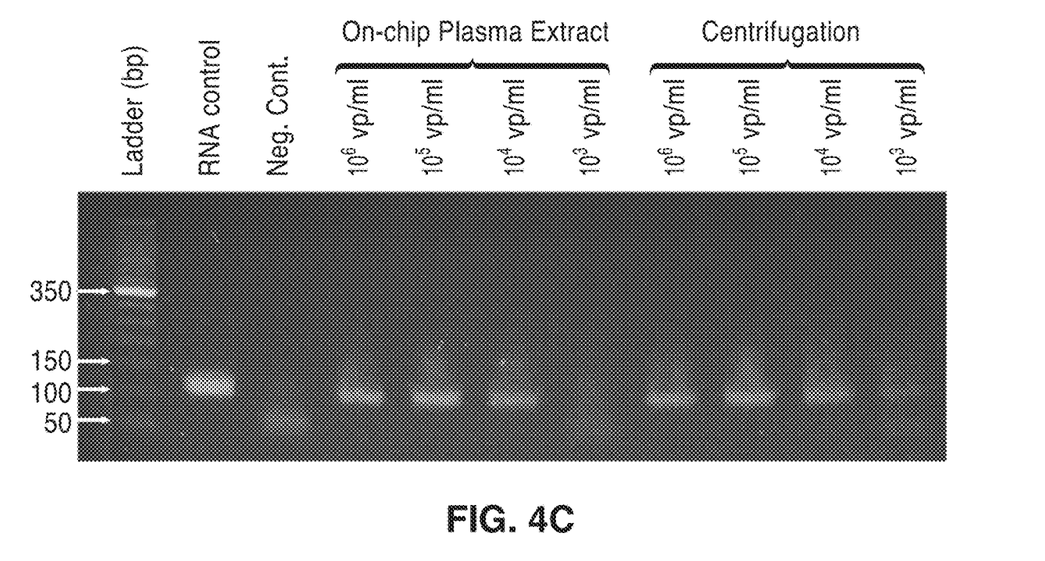
FIG. 4C is an image of a 2% agarose gel result demonstrating the formation of product during RT-qPCR with blood plasma separated by the on-chip plasma separation device in accordance with the present description and conventional centrifugation method.

To investigate the selective Dengue virus separation from the whole blood, the whole blood plasmas containing different concentrations of the Dengue virus were separated using the conventional off-chip centrifugation and on-chip blood plasma separation device. After blood plasma separation, the viral RNA was extracted and RT-qPCR was performed. FIG. 4A shows the real-time fluorescent intensities for the RT-qPCR of Dengue virus. The RT-qPCR with blood plasma separated by on-chip method shows similar threshold cycles with blood plasma prepared by conventional centrifugation method as shown in FIG. 4B. FIG. 4C shows the 2% agarose gel result confirming the formation of the specific PCR products during RT-qPCR with blood plasma containing different concentrations of the Dengue virus. The viral particles recovery can be further improved by optimizing the surface passivation of the plastic surface of the iMDx 10.

Example 3

Figure 5A:
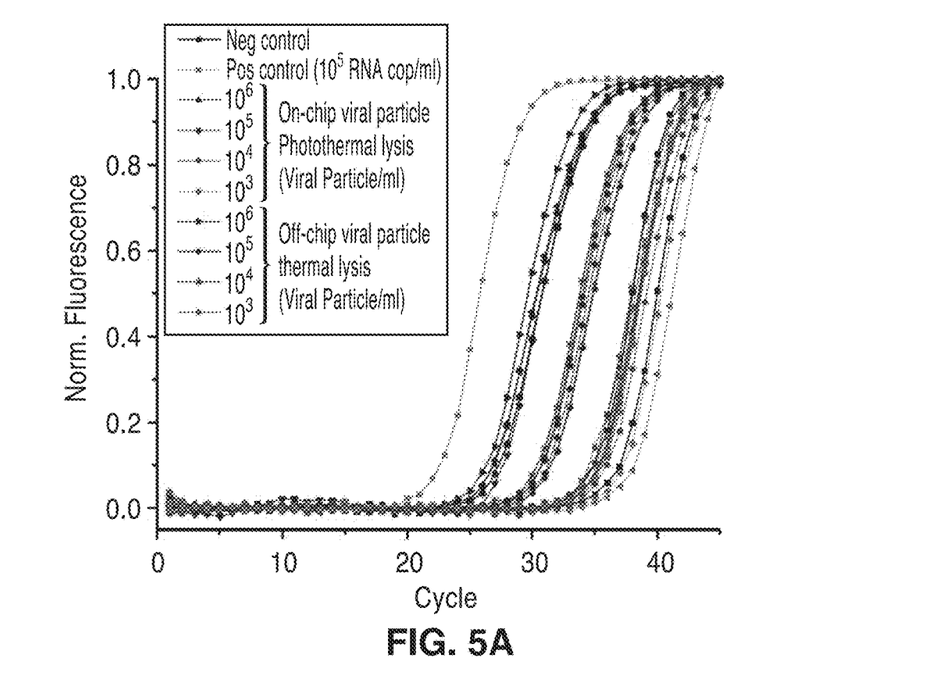
FIG. 5A is a plot showing real-time fluorescent intensity for the RT-qPCR using blood plasma spiked with different concentrations of the Dengue viral particles. The blood plasmas were separated by the conventional centrifugation method and on-chip blood plasma separation device of the present description.
Figure 5B:
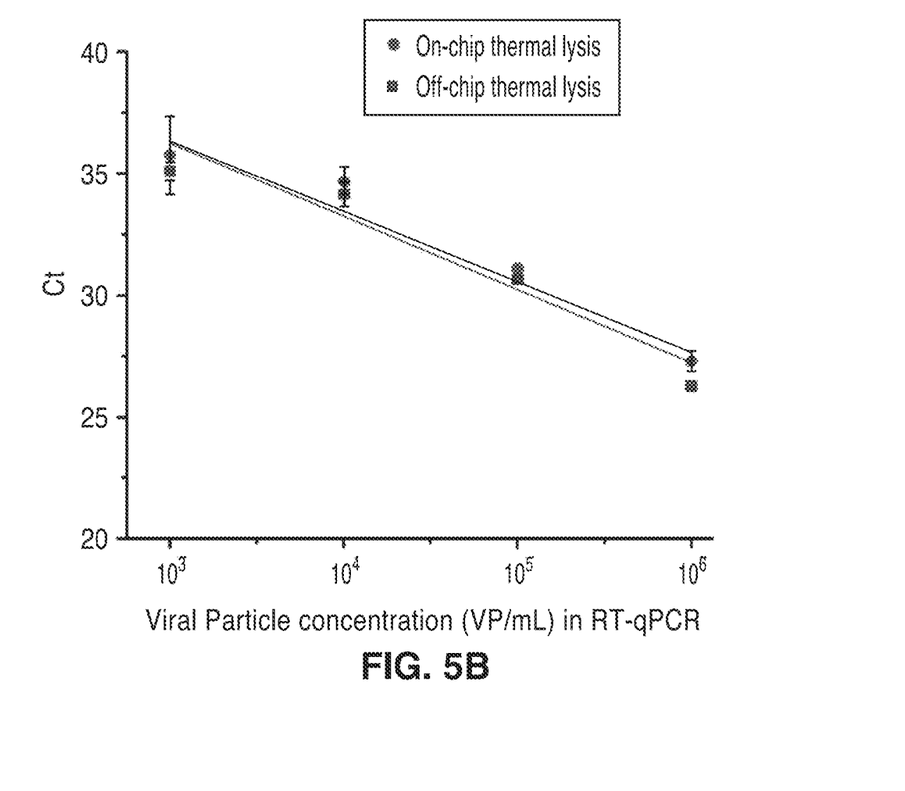
FIG. 5B is a plot summarizing the threshold cycle ($C_t$) for the RT-qPCR using blood plasma prepared with different methods.
Figure 5C:
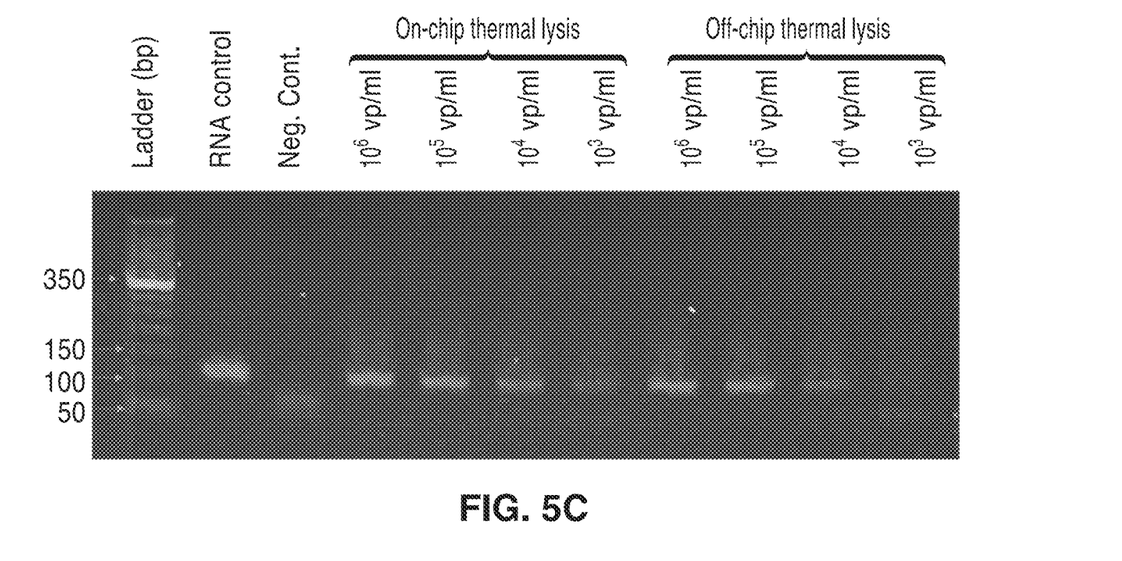
FIG. 5C is an image of 2% agarose gel results demonstrating the formation of product during RT-qPCR with blood plasma separated by the on-chip plasma separation device of the present description and conventional centrifugation method.

An on-chip LED-driven photothermal lysis in optical cavity chamber with two thin gold films (10 nm and 120 nm thicknesses) was also performed as shown in FIG. 5. The blood plasmas containing different concentrations of the Dengue virus were thermally treated to extract the viral RNA. For the comparison purpose, the Bio-Rad PCR thermal cycler was used for the off-chip thermal lysis. As shown in FIG. 5B and FIG. 5C, the on-chip LED-driven photothermal lysis shows the similar results with the off-chip thermal lysis, indicating that this on-chip thermal lysis can effectively extract the viral RNA from Dengue virus for the sample-to-answer molecular diagnostics device at point-of-care.

Figure 6:
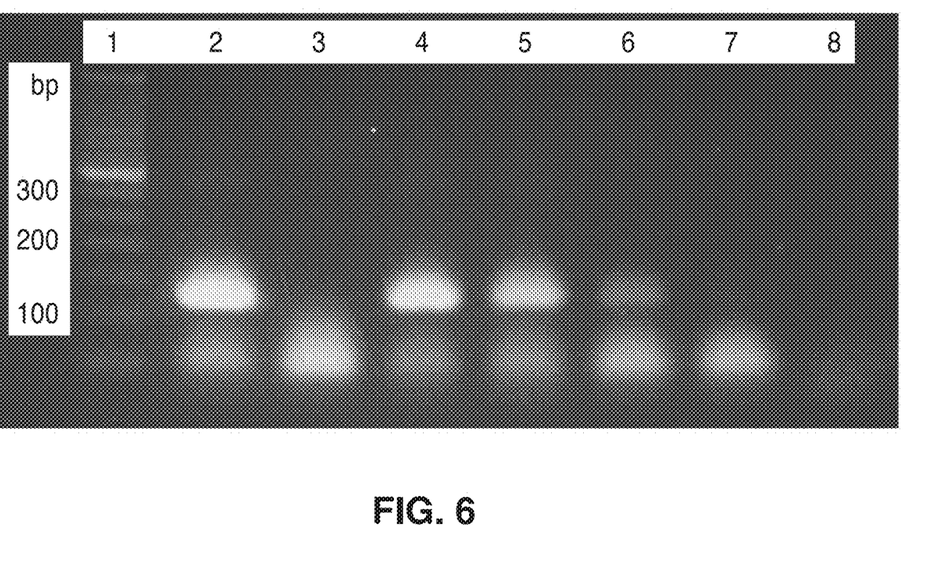
FIG. 6 is an image of 2% agarose gel results demonstrating the formation of product from the rapid optical cavity PCR with different concentration of Dengue cDNA template.

Finally, the LED-driven rapid optical cavity PCR was employed to amplify the Dengue cDNA as shown in FIG. 6. The optical cavity with 10 nm and 120 nm thicknesses was used for the PCR. The amplification of Dengue cDNA template was successfully demonstrated with concentrations ranging from $10^3$ to $10^6$ copies per mL.

From the description herein, it will be appreciated that that the present disclosure encompasses multiple embodiments which include, but are not limited to, the following:

1. An integrated molecular diagnostics system in the form of a micro-fluidic chip for point-of-care diagnosis of a blood sample, the system comprising; a sample inlet at a first location within the micro-fluidic chip, the sample inlet configured for receiving a blood sample; a blood plasma separation chamber located at a second location on the micro-fluidic chip, the blood plasma separation chamber being in fluid communication with the sample inlet to receive the blood sample and separate red blood cells from blood plasma; a photothermal lysis chamber located at a third location on the micro-fluidic chip, the photothermal lysis chamber being in fluid communication with the blood plasma separation chamber to receive the separated blood plasma and perform RNA extraction of the separated blood plasma; and an optical PCR cavity located at a fourth location on the micro-fluidic chip, the optical PCR cavity configured for the amplification of RNA within the separated blood plasma.

2. A method for point-of-care diagnosis of a blood sample, the method comprising; receiving a blood sample at an inlet of a micro-fluidic chip; separating red blood cells from blood plasma in a separation chamber in the micro-fluidic chip, the separation chamber being in fluid communication with the inlet; receive the separated blood plasma within a photothermal lysis chamber located in fluid communication with the separation chamber in the micro-fluidic chip and performing RNA extraction of the separated blood plasma; and receive the separated blood plasma within an optical PCR cavity located in fluid communication with the photothermal lysis chamber in the micro-fluidic chip and amplifying the extracted RNA within the separated blood plasma.

3. An integrated molecular diagnostics system in the form of a micro-fluidic chip for point-of-care diagnosis of a blood sample, the system comprising; a sample inlet at a first location within the micro-fluidic chip, the sample inlet configured for receiving a blood sample; a blood plasma separation chamber located at a second location on the micro-fluidic chip, the blood plasma separation chamber being in fluid communication with the sample inlet to receive the blood sample and separate red blood cells from blood plasma; a photothermal lysis chamber located at a third location on the micro-fluidic chip, the photothermal lysis chamber being in fluid communication with the blood plasma separation chamber to receive the separated blood plasma and perform RNA extraction of the separated blood plasma; and an optical PCR cavity located at a fourth location on the micro-fluidic chip, the optical PCR cavity configured for the amplification of RNA within the separated blood plasma; wherein the optical PCR cavity comprises at least one micro-fluidic thermal cycling chamber, said chamber defined by a plurality of chamber walls configured to hold the blood sample.

4. An integrated molecular diagnostics system for point-of-care diagnosis of Dengue Fever, the system comprising; an on-chip blood plasma separation chamber for the selective separation of a Dengue virus from whole blood within a blood sample; an on-chip LED-driven photothermal lysis chamber for RNA extraction of the Dengue virus; and an on-chip LED-driven rapid optical PCR cavity for the amplification of Dengue viral RNA.

5. A method for point-of-care diagnosis of Dengue Fever, the method comprising; separating blood plasma containing the Dengue virus using hemolysis-free blood plasma separation; heating the separated blood plasma to extract the viral RNA from the virus by LED-driven photothermal lysis; and the amplifying the extracted viral RNA via on-chip LED-driven rapid optical cavity PCR.

6. The system or method of any preceding or subsequent embodiment: wherein the blood sample contains virus; wherein the photothermal lysis chamber is configured for RNA extraction of the virus; and wherein amplification of viral RNA using optical PCR cavity is configured for amplification of viral RNA within the separated blood plasma.

7. The system of any preceding embodiment, wherein the optical PCR cavity comprises at least one micro-fluidic thermal cycling chamber, said chamber defined by a plurality of chamber walls configured to hold the blood sample.

8. The system or method of any preceding or subsequent embodiment, wherein the optical PCR cavity comprises a thin metallic film at a surface of the optical cavity, the thin metallic film configured for heating the separated blood plasma for PCR amplification of target nucleic acid.

9. The system or method of any preceding or subsequent embodiment, wherein the thin metallic film comprises gold.

10. The system or method of any preceding or subsequent embodiment, wherein the thin gold film functions as an LED-driven photothermal heating device.

11. The system or method of any preceding or subsequent embodiment, wherein the photothermal lysis chamber comprises a second thin metallic film at a surface of the photothermal lysis chamber, the second thin metallic film configured for heating the separated blood plasma for performing photothermal lysis.

12. The system or method of any preceding or subsequent embodiment, wherein the second thin metallic film comprises a thin gold film that functions as an LED-driven photothermal heating device.

13. The system or method of any preceding or subsequent embodiment, further comprising: a fluidic pumping mechanism located at a fifth location on the microchip in fluid communication with the optical PCR cavity; the fluidic pumping mechanism configured for drawing the blood sample from the inlet to the optical PCR cavity.

14. The system or method of any preceding or subsequent embodiment, wherein separating red blood cells from blood plasma is performed hemolysis-free.

15. The system or method of any preceding or subsequent embodiment: wherein the blood sample contains virus; wherein performing RNA extraction comprises heating the separated blood plasma to extract the viral RNA from the virus by photothermal lysis; and wherein amplifying the extracted RNA comprises amplifying viral RNA within the separated blood plasma by amplifying the extracted viral RNA via LED-driven rapid optical cavity PCR 16. The system or method of any preceding or subsequent embodiment, wherein photothermal lysis and RNA amplification are LED-driven.

17. The system or method of any preceding or subsequent embodiment, wherein the optical PCR cavity comprises at least one micro-fluidic thermal cycling chamber, said chamber defined by a plurality of chamber walls configured to hold the blood sample.

18. The system or method of any preceding or subsequent embodiment, wherein the optical PCR cavity and photothermal lysis chamber each comprises a thin metallic film, the thin metallic film configured for heating the separated blood plasma for PCR amplification of target nucleic acid and heating the separated blood plasma for performing photothermal lysis.

19. The system or method of any preceding or subsequent embodiment, wherein the thin metallic film comprises gold.

20. The system or method of any preceding or subsequent embodiment, wherein the thin gold film functions as an LED-driven plasmonic heating device.

21. The system or method of any preceding or subsequent embodiment; wherein blood is passively drawn from the inlet to the optical PCR cavity via a fluidic pumping mechanism located on the fluidic microchip in fluid communication with the optical PCR cavity.

22. The system or method of any preceding or subsequent embodiment: wherein the blood sample contains virus; wherein the photothermal lysis chamber is configured for RNA extraction of the virus; and wherein amplification of viral RNA using optical PCR cavity is configured for amplification of viral RNA within the separated blood plasma.

23. The system or method of any preceding or subsequent embodiment, wherein the optical PCR cavity comprises at least one micro-fluidic thermal cycling chamber, said chamber defined by a plurality of chamber walls configured to hold the blood sample.

24. The system or method of any preceding or subsequent embodiment, wherein the optical PCR cavity comprises a pair of thin gold films to form an optical cavity for the photothermal lysis and PCR amplification of target nucleic acid.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An integrated molecular diagnostics system in the form of a micro-fluidic chip for point-of-care diagnosis of a blood sample, the system comprising;
    a sample inlet at a first location within the micro-fluidic chip, the sample inlet configured for receiving a blood sample;
    a blood plasma separation chamber located at a second location on the micro-fluidic chip, the blood plasma separation chamber being in fluid communication with the sample inlet to receive the blood sample and separate red blood cells from blood plasma;
    a photothermal lysis chamber located at a third location on the micro-fluidic chip, the photothermal lysis chamber being in fluid communication with the blood plasma separation chamber to receive the separated blood plasma, wherein the photothermal lysis chamber comprises a first metallic film at a surface of the photothermal lysis chamber, the first metallic film configured to heat the separated blood plasma to perform RNA extraction from the separated blood plasma; and
    an optical PCR cavity located at a fourth location on the micro-fluidic chip, wherein the optical PCR cavity is configured to receive the extracted RNA and to amplify the extracted RNA within the separated blood plasma, wherein the optical PCR cavity comprises a second metallic film at a surface of the optical PCR cavity, the second metallic film configured to perform light-to-heat conversion for PCR amplification of the extracted RNA.

2. The system of claim 1:
    wherein the blood sample contains virus;
    wherein the photothermal lysis chamber is configured for RNA extraction of the virus; and
    wherein amplification of viral RNA using optical PCR cavity is configured for amplification of viral RNA within the separated blood plasma.

3. The system of claim 1, wherein the optical PCR cavity comprises at least one micro-fluidic thermal cycling chamber, said micro-fluidic thermal cycling chamber defined by a plurality of chamber walls configured to hold the blood sample.

4. The system of claim 1, wherein the extracted RNA is a target nucleic acid.

5. The system of claim 1, wherein the second metallic film comprises gold.

6. The system of claim 1, wherein the second metallic film functions as an LED-driven photothermal heating device.

7. The system of claim 1, wherein the first metallic film comprises a gold film that functions as an LED-driven photothermal heating device.

8. The system of claim 1, further comprising:
- a fluidic pumping mechanism located at a fifth location on the micro-fluidic chip in fluid communication with the optical PCR cavity;
- the fluidic pumping mechanism configured for drawing the blood sample from the inlet to the optical PCR cavity.

9. An integrated molecular diagnostics system in the form of a micro-fluidic chip for point-of-care diagnosis of a blood sample, the system comprising:
- a sample inlet at a first location within the micro-fluidic chip, the sample inlet configured for receiving a blood sample;
- a blood plasma separation chamber located at a second location on the micro-fluidic chip, the blood plasma separation chamber being in fluid communication with the sample inlet to receive the blood sample and separate red blood cells from blood plasma;
- a photothermal lysis chamber located at a third location on the micro-fluidic chip, the photothermal lysis chamber being in fluid communication with the blood plasma separation chamber to receive the separated blood plasma, wherein the photothermal lysis chamber comprises a first metallic film at a surface of the photothermal lysis chamber, the first metallic film configured to heat the separated blood plasma to perform RNA extraction from the separated blood plasma; and
- an optical PCR cavity located at a fourth location on the micro-fluidic chip, wherein the optical PCR cavity is configured to receive the extracted RNA and to amplify the extracted RNA within the separated blood plasma;
- wherein the optical PCR cavity comprises at least one micro-fluidic thermal cycling chamber, said micro-fluidic thermal cycling chamber defined by a plurality of chamber walls configured to hold the blood sample, wherein at least one of the plurality chamber walls comprises a second metallic film configured to perform light-to-heat conversion for PCR amplification of the extracted RNA.

10. The system of claim 9:
wherein the blood sample contains virus;
wherein the photothermal lysis chamber is configured for RNA extraction of the virus; and
wherein amplification of viral RNA using optical PCR cavity is configured for amplification of viral RNA within the separated blood plasma.

* * * * *

UNITED STATES PATENT AND TRADEMARK OFFICE
CERTIFICATE OF CORRECTION

PATENT NO. : 11,446,667 B2
APPLICATION NO. : 16/380693
DATED : September 20, 2022
INVENTOR(S) : Luke P. Lee and Jun Ho Son It is certified that error appears in the above-identified patent and that said Letters Patent is hereby corrected as shown below:

On the Title Page

Column 1, Lines 9-10, item (72) change:
"Inventors: Luke P. Lee, Orinda, CA (US); Jun Ho Sun, El Cerrito, CA (US)"

To:
--Inventors: Luke P. Lee, Orinda, CA (US); Jun Ho Son, El Cerrito, CA (US)--

Signed and Sealed this
Twenty-fifth Day of October, 2022

Katherine Kelly Vidal
*Director of the United States Patent and Trademark Office*